United States Patent
Weiland et al.

(10) Patent No.: US 6,881,953 B2
(45) Date of Patent: Apr. 19, 2005

(54) METHOD OF TRACING DRAINS

(75) Inventors: Michael J. Weiland, Sproul, PA (US); John E. Hoots, St. Charles, IL (US)

(73) Assignee: Nalco Company, Naperville, IL (US)

( * ) Notice: Subject to any disclaimer, the term of this patent is extended or adjusted under 35 U.S.C. 154(b) by 349 days.

(21) Appl. No.: 09/966,912

(22) Filed: Sep. 28, 2001

(65) Prior Publication Data

US 2003/0071212 A1 Apr. 17, 2003

(51) Int. Cl.$^7$ ................................. G01P 5/20
(52) U.S. Cl. ................ 250/302; 250/259; 73/861.07
(58) Field of Search ........................ 250/256, 259, 250/302; 73/1.24, 170.04, 861.05, 861.07, 861.95

(56) References Cited

U.S. PATENT DOCUMENTS

| | | | | |
|---|---|---|---|---|
| 3,851,171 A | * | 11/1974 | Saniford et al. | 705/1 |
| 4,145,923 A | * | 3/1979 | McClure | 250/259 |
| 4,620,817 A | * | 11/1986 | Cushing | 73/861.05 |
| 5,304,800 A | | 4/1994 | Hoots et al. | |
| 5,352,244 A | * | 10/1994 | Azok | 435/43 |
| 5,416,323 A | | 5/1995 | Hoots et al. | |
| 5,919,002 A | * | 7/1999 | Ramp | 405/184.2 |
| 6,216,543 B1 | * | 4/2001 | Colin | 73/861.05 |
| 2002/0052755 A1 | * | 5/2002 | Whatley et al. | 705/1 |

OTHER PUBLICATIONS

Sidle, W.C., Lee, P.Y., "Urban Stormwater Tracing with the Naturally Occuring Deuterium Isotope", Water Environment Research, vol. 71, No. 6, pp. 1251–1256, 1999.

Chmielewski, A.G., Dobrowlski, A., Owczarczyk, A., Palige J., "Sedimentation Basin Investigation Using Radiotracers", Institute of Nuclear Chemistry and Technology, Warsaw, Poland, pp. 481–487, 15, 79, 2001.

Roldão, J., Pecly, J., Leal, L., "Tracer techniques to evaluate the dilution performance of sewage submarine outfalls", Water Pollution IV: Modell., Meas. Predict., Int. Conf. 4$^{th}$,pp. 185–194, 1977.

Yager, Richard M., Kappel, William M., "Infiltration and hydraulic connections from the Niagara River to a fractured–dolomite aquifer in Niagara Falls, New York", Journal of Hydrology (Amsterdam), vol. 206, pp. 84–97, 1998.

N.K. Breedin, Jr., J.W. Dawson, "Pros and Cons of Storm Water Recharge Wells", Water & Sewage Works, pp. 82–84, 1977.

Cole–Parmer Instrument Catalog, p. 1337, 1997–1998.

H.S. Stuttman Inc. Publishers, Westport, Connecticut, The New Illustrated Science and Invention Encyclopedia, "Pipeline", pp. 1949–1950, "Plumbing", pp. 1989–1992, "Drainage", pp. 743–746, 1989.

John E. Hoots, "Practical Applications of Tracers—Beyond Product Monitoring", Presented at the 1990 Cooling Tower Institute Annual Meeting, Houston, Texas, Feb. 5–7, 1990.

* cited by examiner

*Primary Examiner*—Albert Gagliardi
(74) *Attorney, Agent, or Firm*—Michael B. Martin; Thomas M. Breininger

(57) ABSTRACT

The claimed method of tracing drains starts with a comprehensive building survey in which all existing drains are numbered. A Master Blueprint and a Master Spreadsheet are created using information collected in the building survey. A tracer is used to determine the flow of storm water to and from the building's storm drains. A test location, consisting of a storm manhole or a sanitary manhole is then chosen and water is run continuously through this manhole. A non-toxic fluorescent tracer is added to the target sanitary drain and a sample of the water running through the test location is withdrawn. A fluorometer is used to detect the fluorescent signal of non-toxic fluorescent tracer in the sample of water withdrawn. This procedure is repeated until all test locations have been surveyed and the information recorded on the Master Blueprint and Master Spreadsheet. The information is used to replumb drains.

20 Claims, No Drawings

METHOD OF TRACING DRAINS

FIELD OF INVENTION

This invention is in the field of drains and drainage systems. Specifically, this invention is in the field of tracing of drains to determine where the drains lead.

BACKGROUND OF THE INVENTION

The New Illustrated Science and Invention Encyclopedia, © 1987, 1989 by Marshall Cavendish Limited has articles on Plumbing (pp. 1989–1992), Pipelines (pp. 1949–1950), and Drainage (pp. 743–746) which give a good background, with illustrations, concerning how drainage systems are set up and how they work and also describe the components of a working drainage system.

Most buildings have a minimum of at least two different types of drainage systems; a storm drainage system and a sanitary, also known as the sewage, drain system. There are certain facilities (and/or buildings within that facility) that have a third drainage system. This third drainage system drains process waters into onsite holding tanks where the process water is treated before it is discharged off of the facility property or it is hauled away as waste that is to be dealt with outside the municipal sewage treatment system.

The storm drainage system is designed to convey rainwater and other forms of precipitation. Water collected from such precipitation is water in its purest form. This water should contain no contaminants. Because of this, storm drainage water can be discharged (untreated) into streams, rivers, lakes or the ground (water disposal via percolation). The storm water system collects water from roof drains and some drains outside the building which collect water runoff from parking lots, sidewalks, lawns, etc. Storm drains convey water into a storm manhole and other drains which are typically routed to natural bodies of water or to the ground. Storm drains are not typically routed to the sewer system and from there to the sewage treatment plant because, being natural precipitation, the material in a storm drain is not considered "contaminated" such that it needs treatment. Furthermore, the volume of storm water is such that if all the rainwater collected was routed to the sewage treatment system, the sewage treatment system would probably be overwhelmed and in order to prevent flooding, untreated sewage would have to be released. This release of untreated sewage is undesirable from an environmental point of view as well as from a legal point of view. It is undesirable from an environmental point of view as raw sewage is not good for any natural ecosystem. It is undesirable from a legal point of view as there are specific laws which prohibit such actions from taking place.

In contrast to storm drainage systems, sanitary drains are designed to drain material into a sewage treatment system and from there the material in the sewage treatment system is conveyed to the sewage treatment plant for treatment.

Problems occur when storm drains are mistakenly cross-connected to sanitary piping. The most serious difficulty occurs whenever heavy amounts of precipitation happen during a relatively short amount of time leading to an excess amount of water being forced through cross-connections into the sanitary piping, where the excess water ends up in the sewage treatment system. This leads to the undesirable situation where the sewage treatment plant has to discharge untreated sewage in order to avoid having their system become overwhelmed with excess water. This discharge of untreated sewage usually puts the sewage treatment plant out of compliance with local, state and Federal water quality laws and regulations.

Problems also occur when sanitary drains are mistakenly cross-connected to storm piping. There is nothing good about the prospect of having untreated sewage present in drains designed to convey only rain water or melted snow. When sewage is present is the storm water system it is considered a "release of untreated sewage" into the environment. This release of untreated sewage is undesirable from an environmental point of view as well as from a legal point of view. It is undesirable from an environmental point of view as raw sewage reeks havoc on the ecosystem downstream. It is undesirable from a legal point of view as there are specific laws that prohibit discharge of untreated sewage and provide for legal sanctions against the building owners as being responsible for causing the release.

Cross-connections of storm drains into sanitary drainage systems and cross-connections of sanitary drains into storm drainage systems are a fact of life in modern society. Finding these cross-connections and fixing them is a responsibility of property owners. Another reality is that the current building owners are not always the same as the people who owned the building when it was built and the plumbing installed. Therefore the current building owners are not always in the best position to understand how the plumbing in the building was installed in the first place.

It is understood that it is standard procedure in designing the plumbing in a new building or even working on the plumbing in an existing building to have blueprints showing each and every pipe and each and every drainage line and where it is supposed to drain. However, it is often true that the paperwork showing where the drains are and where they drain to, does not always match the reality of where the drains are and where they drain. Therefore, methods of tracing drains to determine where material in a drain ends up are often needed to be used to determine where the existing drains are draining.

Current known methods of tracing drains to find out where the material in the drain drains to include a method known as the "Hot Water" method. Because storm water is normally cool (from about 55° F. to about 90° F.), hot water (water at a temperature greater than 100° F.) can be added to each floor drain at a continuous rate. This hot water can then be "looked for" at a storm water manhole by using a remote thermometer to register the actual temperature of the water, noting any sudden increase in the temperature of the water. The advantage of this method is that it is very non-expensive.

The disadvantage of this "Hot Water" method is that it is not very conclusive. If there were only one "cross-connected" drain in a building (and this was known beforehand) this method might work adequately. However, the "Hot Water" method cannot conclusively prove that any one drain was bad because there could be other reasons why the temperature of the water might be elevated. For example, if a sink, which just happened to have hot water running, were to be plumbed to the storm water drain, and if that sink were running during the time another drain was being tested, this would skew the results.

Other known current methods to determine where drains drain to, require the use of visible dyes, other types of dyes, and/or radioactive materials that are detectable either by sight or by the use of an analytical instrument such as, but not limited to, a Geiger counter. In the following table, the use listed for each dye is one example of a suitable use for the visible dye, other types of dye, and/or radioactive materials.

TABLE

| Substance | Use |
| --- | --- |
| (1) Brilliant Blue dye | field irrigation tracing |
| (2) Bromide | field irrigation tracing |
| (3) Bromide | tile drains for fields |
| (4) Chloride | groundwater, subsurface drains |
| (5) Deuterium isotope | storm sewers* |
| (6) Radionuclides | sewer discharge** |
| (7) $O^{18}$ isotope | groundwater*** |
| (8) Lithium chloride | streams/mine drainage |
| (9) Fluorescent tracers | sewage discharge into seawater****, hydrological studies of aquifers, streams, rivers, etc. |
| (10) Metal ions (e.g., lithium) | hydrological studies of aquifers, streams, rivers, etc. |
| (11) Bacteria | hydrological studies of aquifers, streams, rivers, etc. |

*as described in "Urban Stormwater Tracing with the Naturally Occurring Deuterium Isotope", by Sidle et al., Water Environ. Res. 71(6), pp. 1251–1256 © 1999.
**as described in "Sedimentation Basin Investigation Using Radiotracers" by Chmielewski et al, Institute of Nuclear Chemistry and Technology, Warsaw, Poland, 15, 79, pp. 481–487, © 2001.
***as described in "Infiltration and Hydraulic Connections from the Niagara River to a Fractured-Dolomite Aquifer in Niagara Falls, New York", by Yager et al., J. Hydrol. (Amsterdam), 206(1–2), pp. 84–97, © 1998.
****as described in "Tracer Techniques to Evaluate the Dilution Performance of Sewage Submarine Outfall", by Roldao et al, Water Pollution IV: Modell., Meas. Predict., Int. Conf., 4$^{th}$, pp. 185–194 (1997).

Materials indicated above are available from many sources, including Norlab Inc., P.O. Box 380, Amherst, Ohio 44001 USA (telephone no. 1-800-247-9422).

The currently known visible dyes, other types of dyes and radioactive tracer materials require either visible review of the material in the drain, leading to labor-intensive and sometimes dangerous positioning of workers in difficult-to-reach locations (such as being face down in the middle of a street looking into a manhole with a flashlight) in order to look for visible dye, or the use of analytical devices, or the use of radioactive materials and Geiger counters, which are not always desirable to use around people and animals.

Furthermore, it is usually never desirable to use a visible dye in circumstances where the change in color of the water can be noticed and commented on by the general public.

The article, "Practical Applications of Tracers—Beyond Product Monitoring, by John E. Hoots, Presented at the 1990 Cooling Tower Institute Annual Meeting in Houston, Tex. on Feb. 5–7, 1990, describes the addition of very low concentrations of a chemical tracer to cooling water systems in order to be able to quantify previously unaccounted blowdown, leakage, time of travel of cooling water to nearby waterways, and out-of-specification operating conditions.

U.S. Pat. No. 5,304,800, issued Apr. 19, 1994 to Hoots et al., describes and claims a process for detecting leakage from a process fluid to a temperature-conditioning fluid in an industrial process using a "tracer chemical".

It would be desirable to have a method of determining where drains lead that offers an alternative to the labor-intensive use of visible dyes or of radioactive materials.

SUMMARY OF THE INVENTION

The first aspect of the claimed invention is a method of tracing drains in a building comprising:
(1) surveying the building to locate all existing drains;
(2) numbering all of the existing drains;
(3) creating a Master Blueprint and a Master Spreadsheet showing all of the drains;
(4) using a tracer to determine whether the storm water from the building actually flows from each storm drain to the storm water manhole and recording the information determined about the flow pattern of each storm drain tested on the Master Blueprint and on the Master Spreadsheet;
(5) selecting the test location to withdraw the sample of water, wherein said test location is selected from the group consisting of all storm manholes and all sanitary manholes;
(6) running water continuously through a drain that drains into the test location manhole selected in Step (5);
(7) selecting a target sanitary drain and adding an amount of non-toxic fluorescent tracer to the target sanitary drain, wherein the amount of non-toxic fluorescent tracer added is such that the fluorescent signal of non-toxic fluorescent tracer is detectable over the background fluorescence of the water in said sanitary drain;
(8) using a fluorometer to detect the fluorescent signal of said non-toxic fluorescent tracer in the sample of water withdrawn at the test location selected in Step (5);
(9) using the fluorescent signal to determine whether the target sanitary drain is draining to the test location selected in Step (5) and recording the information determined about the flow pattern of said target sanitary drain on the Master Blueprint and on the Master Spreadsheet;
(10) repeating Steps (4), (5), (6), (7), (8) and (9) as necessary such that all sanitary drains are traced; and
(11) using the information from the Master Blueprint and Master Spreadsheet to determine where all sanitary drains and storm drains are draining.

The second aspect of the claimed invention is a method of tracing drains in a building comprising:
(1) surveying the building to locate all existing drains;
(2) numbering all of the existing drains;
(3) creating a Master Blueprint and a Master Spreadsheet showing all of the drains;
(4) using a tracer to determine whether the storm water from the building actually flows from each storm drain to the storm water manhole and recording the information determined about the flow pattern of each storm drain tested on the Master Blueprint and on the Master Spreadsheet;
(5) selecting the test location to withdraw the sample of water, wherein said test location is selected from the group consisting of all storm manholes and all sanitary manholes;
(6) running water continuously through a drain that drains into the test location manhole selected in Step (5);
(7) selecting a target sanitary drain and adding an amount of non-toxic fluorescent tracer to the target sanitary drain, wherein the amount of non-toxic fluorescent tracer added is such that the concentration of non-toxic fluorescent tracer is at least about 600 ppm in the water in said target sanitary drain;
(8) using a fluorometer to detect the fluorescent signal of said non-toxic fluorescent tracer in the sample of water withdrawn at the test location selected in Step (5);
(9) using the fluorescent signal to determine whether the target sanitary drain is draining to the test location selected in Step (5) and recording the information determined about the flow pattern of said target sanitary drain on the Master Blueprint and on the Master Spreadsheet;
(10) repeating Steps (4), (5), (6), (7), (8) and (9) as necessary such that all sanitary drains are traced; and
(11) using the information from the Master Blueprint and Master Spreadsheet to determine where all sanitary drains and storm drains are draining.

The third aspect of the claimed invention is a method of tracing drains of interest in a building comprising:

(1) surveying the building to locate the drains of interest;
(2) numbering all of the drains of interest;
(3) creating a Master Blueprint and a Master Spreadsheet showing all of the drains of interest;
(4) using a tracer to determine whether the storm water from the building actually flows from the storm drains of interest to the storm water manhole and recording the information determined about the flow pattern of each storm drain tested on the Master Blueprint and on the Master Spreadsheet;
(5) selecting the test location to withdraw the sample of water, wherein said test location is selected from the group consisting of all storm manholes and all sanitary manholes;
(6) running water continuously through a drain that drains into the test location manhole selected in Step (5);
(7) selecting a target sanitary drain of interest and adding an amount of non-toxic fluorescent tracer to the target sanitary drain of interest, wherein the amount of non-toxic fluorescent tracer added is such that the fluorescent signal of non-toxic fluorescent tracer is detectable over the background fluorescence of the water in said target sanitary drain of interest;
(8) using a fluorometer to detect the fluorescent signal of said non-toxic fluorescent tracer in the sample of water withdrawn at the test location selected in Step (5);
(9) using the fluorescent signal to determine whether the target sanitary drain of interest is draining to the test location selected in Step (5) and recording the information determined about the flow pattern of said target sanitary drain of interest on the Master Blueprint and on the Master Spreadsheet;
(10) repeating Steps (4), (5), (6), (7), (8) and (9) as necessary such that all sanitary drains of interest are traced; and
(11) using the information from the Master Blueprint and Master Spreadsheet to determine where the sanitary drains of interest and the storm drains of interest, are draining.

The fourth aspect of the claimed invention is a method of tracing drains of interest in a building comprising:

(1) surveying the building to locate the drains of interest;
(2) numbering all of the drains of interest;
(3) creating a Master Blueprint and a Master Spreadsheet showing all of the drains of interest;
(4) using a tracer to determine whether the storm water from the building actually flows from the storm drains of interest to the storm water manhole and recording the information determined about the flow pattern of each storm drain tested on the Master Blueprint and on the Master Spreadsheet;
(5) selecting the test location to withdraw the sample of water, wherein said test location is selected from the group consisting of all storm manholes and all sanitary manholes;
(6) running water continuously through a drain that drains into the test location manhole selected in Step (5);
(7) selecting a target sanitary drain of interest and adding an amount of non-toxic fluorescent tracer to the target sanitary drain of interest, wherein the amount of non-toxic fluorescent tracer added is such that the concentration of non-toxic fluorescent tracer is at least about 600 ppm in the water in said target sanitary drain of interest;
(8) using a fluorometer to detect the fluorescent signal of said non-toxic fluorescent tracer from the sample of water withdrawn at the test location selected in Step (5);
(9) using the fluorescent signal to determine whether the target sanitary drain of interest is draining to the test location selected in Step (5) and recording the information determined about the flow pattern of said target sanitary drain of interest on the Master Blueprint and on the Master Spreadsheet;
(10) repeating Steps (4), (5), (6), (7), (8) and (9) as necessary such that all sanitary drains of interest are traced;
(11) using the information from the Master Blueprint and Master Spreadsheet to determine where the sanitary drains of interest and the storm drains of interest are draining.

DETAILED DESCRIPTION OF THE INVENTION

Throughout this patent application the following terms have the indicated definitions:

"aka" means "also known as".

ALDRICH refers to Aldrich, P.O. Box 355, Milwaukee, Wis. 53201 USA., telephone number (800) 558-9160.

CAS Registry No. refers to the Chemical Abstracts Service Registry No. for a compound.

LANCASTER refers to Lancaster Synthesis Inc., P.O. Box 1000, Windham, N.H. 03087-9977, telephone number (800) 238-2324.

Nalco refers to ONDEO Nalco Company, ONDEO Nalco Center, 1601 W. Diehl Road, Naperville Ill. 60563, telephone number (630) 305-1000.

The first step in the instant claimed invention is to survey the selected building to locate all the existing drains. The survey can include all of the drains in the building, or if desired, the survey can include only those drains of interest. When reporting the results of this method, it is important to note whether all of the drains in the building were surveyed and tested, or whether the method surveyed and tested drains of interest only.

This survey typically begins with reviewing the blueprints for the building. Preferably the blueprints reviewed should be those labeled "As Built" as compared to those labeled "Proposed" because, as is known to ordinary people of skill in the art of blueprints, the "As Built" blueprints better reflect the actual structure that was built. Whatever blueprints are available, the blueprint with the best information should be chosen as the basis for the "Master Blueprint" and for the "Master Spreadsheet" that are to be created by following the method of the instant claimed invention.

If no blueprints are available for review, then the survey of the building to physically locate the drains and pipes will be the first step in the creation of a "Master Blueprint" and "Master Spreadsheet". The Master Blueprint is created to show where all the drains are by representing the drains pictorially, whereas the Master Spreadsheet is created to show written information about each drain, when it was tested and what the results of the tests were.

After the blueprints have been reviewed or it has been determined that there are no blueprints to review, the survey process continues with an on-site inspection of the building. All drains need to be physically located--from the roof to the basement. The inspection typically, though not always, starts with the roof and proceeds downward through the building. All drains located should be checked against the best available blueprint and the actual location of the drains and any discrepancy between the blueprint and the actual building should be noted on the Master Blueprint and Master Spreadsheet that are being created during the method of the instant claimed invention.

In surveying the building for drains, examples of drains to be noted on the blueprint include sinks, floor drains, urinals, toilets, cup drains, roof drains, cooling tower overflows, cooling tower blowdowns, outside storm drains, and water fountains. If any drain is believed to be covered for any reason (carpet, raised floor, etc), the covered drain is marked down and noted as such, so that if the drain is ever uncovered, the Master Blueprint and Master Spreadsheet will both show that at the point in time the method of the instant claimed invention was conducted this particular drain was unable to be tested due to limited access.

It is recommended, though not required, that the different types of drains and pipes be marked down with their own particular symbol to make it easier to distinguish between them. There are as many different symbols for drains and pipes as there are people working on blueprints. All symbols are acceptable as long as they are unambiguous. One set of acceptable useful symbols for certain drains and process piping is the following:

| Symbol | Meaning |
| --- | --- |
| ● | manhole or m.h |
| ○ | cleanout or c.o. |
| ◉ | downspout (roof drain) |
| ■ | floor drain or f.d. |
| ¤ | catch basin or c.b. |
| ▫ | sink |
| ——————— | sanitary sewer |
| - - - - - - - - - - - - | process sewer (underground) |
| — — — — — — | process sewer (above ground) |
| —·—·—·—·— | storm sewer |
| —LW—LW—LW—LW— | lab waste |

When the use of additional specific identification symbols for "specialized" drains becomes necessary or desirable, then individual symbols for specific drains can be created by the method operator. The only criteria for selection and use of these symbols is that a master "key" be kept readily available, so people not familiar with the method of the instant claimed invention can still read and understand where each drain is and what material is supposed to be draining through the drain.

Step two in the method of the instant claimed invention is to unambiguously number all of the drains and use the unambiguous number for each drain to input the drain identification onto a Master Spreadsheet listing all of the drains in the building. There are as many different ways to unambiguously number the drains as there are people working with drains. One acceptable method of numbering the drains is as follows. The drains are first numbered on the blueprint starting with one and increasing until the last drain has been counted. The numbering starts in the lowest room number. The drains are counted in increasing order starting with the most northern drain in that room and then reading from west to east. The next higher room number will be next, and this procedure will be followed until all of the rooms are completed and all the drains are numbered.

After all the drains have all been numbered, Step (3) in the process of the instant claimed invention is to use the information gathered in Step (1) and Step (2) to create the Master Spreadsheet and the Master Blueprint. The Master Blueprint and the Master Spreadsheet will be used throughout the remainder of the method as the repositories for the information collected.

One acceptable layout for a Master Spreadsheet is as follows.

TABLE I

Master Spreadsheet

| Drain # | Nomenclature | Time dye added | Test # | Results of test |
| --- | --- | --- | --- | --- |
| 1 | Fuzzybldg-002-S-A | 8:37 a | 2 | |
| 2 | Fuzzybldg-002-FD-A | 8:40 a | 2 | |
| 3 | Fuzzybldg-002-S-B | 8:44 a | 2 | |
| 4 | Fuzzybldg-002-FD-B | 8:45 a | 2 | |
| 5 | Fuzzybldg-003-FD-A | 8:51 a | 2 | |
| 6 | Fuzzybldg-003-S-A | 8:53 a | 2 | |
| 7 | Fuzzybldg-005-S-A | 8:55 a | 2 | |

It is to be noted, that each drain included in the Master Spreadsheet has been named using a particular nomenclature suitable for unambiguously identifying drains and their relative position within the target building, the building being identified as "Fuzzybuilding" or "Fuzzybldg" for purposes of this patent application. This nomenclature allows each drain to be unambiguously identified compared to all of the other tested drains. The following table gives one possible type of nomenclature for the drains, with the nomenclature being used being very descriptive. The nomenclature selected was chosen to give the building name, room number, drain type, and an individual drain letter for each drain:

TABLE II

Nomenclature for Drain Identification
Using this as the pattern for drain identification
Building - Room # - Drain Type - Drain Letter

| Abbreviation | Drain Type |
| --- | --- |
| FD | Floor Drain |
| RD | Roof Drain |
| CD | Cup Drain |
| TO | Cooling Tower Overflow |
| TB | Cooling Tower Blowdown |
| OD | Outside Storm Drain |
| WF | Water Fountain |
| T | Toilet |
| S | Sink |
| UR | Urinal |

The drain letter is assigned in an order in the same manner as the drain number (furthest north, read west to east). The drain letters are specific to the particular type of drains. So if there were, for example, two sinks and one floor drain in room 104 of Smoothbldg, the nomenclature of the three drains would be Smoothbldg-104-S-A;

Smoothbldg-104-S-B; and

Smoothbldg-104-FD-A.

Some drains will not easily fit into this or any other numbering system. For instance, if a drain is missed while surveying and found during testing, or if the drain had been added between surveying and testing, the drain will not be able to be numbered according to the method described above without changing the numbers of all of the drains after it. To eliminate renumbering the drains every time a new drain is found, the newly discovered drain can be numbered one higher than the drain with the previous highest number designation. If this procedure is followed, although a drain may not sequentially fit into the pattern of drain nomenclature identified previously, all of the drains will always be clearly marked on the Master Blueprint and Master Spreadsheet.

The fourth step in the process of the instant claimed invention is using a tracer to determine whether the storm water from the building actually flows from each storm drain to the storm water manhole and recording the information determined about the flow pattern of each storm drain tested on the Master Blueprint and on the Master Spreadsheet. It is typically the case that not all storm drains drain into the storm water drainage system. Instead of draining into the storm water drainage system, some storm drains drain into percolating ditches and eventually drain directly into the ground. Other storm drains simply drain directly into the ground. Therefore, the need for the fourth step in the process of the instant claimed invention is to determine whether the storm water from the building draining from roof drains and even outside storm drains actually flows from each storm drain to the storm water manhole as designed. This is done to help prevent any storm system serving the building from being untested.

Step (4) can be conducted using any of the known test methods for tracing drains. Known test methods include visual dyes such as, but not limited to, fluoroscein (aka yellow/green dye) and rhodamine WTS (aka red dye). These dyes are available from many standard chemical or chemical instrument supply companies, including the Cole-Parmer Instrument Company, (800) 323-4340.

The test for storm water is typically conducted by tracing the main storm drain that is supposed to lead to the storm water manhole or manholes that was or were designed to pick up all of the buildings' storm water. The test is conducted by placing the supplier's recommended amount of visible dye in the storm drain and looking for the color of the dye in the storm water manhole. This is done for each storm drain, usually using different colors of dye or waiting for enough time to pass to have the color of the dye "clear out" of the storm manhole.

An alternative to the use of visible dyes to trace the storm drains, is the use of a non-toxic fluorescent tracers. Suitable non-toxic fluorescent tracers are selected from the group consisting of Acridine Orange (CAS Registry No. 65-61-2),
2-anthracenesulfonic acid, sodium salt (CAS Registry No. 16106-40-4),
Anthrasol Green IBA (CAS Registry No. 2538-84-3, aka Solubilized Vat Dye),
bathophenanthrolinedisulfonic acid disodium salt (CAS Registry No. 52746-49-3),
amino 2,5-benzene disulfonic acid (CAS Registry No. 41184-20-7),
2-(4-aminophenyl)-6-methylbenzothiazole (CAS Registry No. 92-36-4),
Brilliant Acid Yellow 8G (CAS Registry No. 2391-30-2, aka Lissamine Yellow FF, Acid Yellow 7),
Celestine Blue (CAS Registry No. 1562-90-9),
cresyl violet acetate (CAS Registry No. 10510-54-0),
dibenzofuransulfonic acid, 1-isomer (CAS Registry No. 42137-76-8),
dibenzofuransulfonic acid, 2-isomer (CAS Registry No. 257627-62-2),
1-ethylquinaldinium iodide (CAS Registry No. 606-53-3),
fluorescein (CAS Registry No. 2321-07-5)
fluorescein, sodium salt (CAS Registry No. 518-47-8, aka Acid Yellow 73, Uranine),
Keyfluor White ST (CAS Registry No. 144470-48-4, aka Flu. Bright. 28),
Keyfluor White CN (CAS Registry No. 16470-24-9),
Leucophor BSB (CAS Registry No. 68444-86-0, aka Leucophor AP, Flu. Bright. 230),
Leucophor BMB (CAS Registry No. 16470-24-9, aka Leucophor U, Flu. Bright. 290),
Lucigenin (CAS Registry No. 2315-97-1, aka bis-N-methylacridinium nitrate),
mono-, di-, or tri-sulfonated napthalenes, including but not limited to
  1,5-naphthalenedisulfonic acid, disodium salt (hydrate) (CAS Registry No. 1655-29-4, aka 1,5-NDSA hydrate),
  2-amino-1-naphthalenesulfonic acid (CAS Registry No. 81-16-3),
  5-amino-2-naphthalenesulfonic acid (CAS Registry No. 119-79-9),
  4-amino-3-hydroxy-1-naphthalenesulfonic acid (CAS Registry No. 90-51-7),
  6-amino-4-hydroxy-2-naphthalenesulfonic acid (CAS Registry No. 116-63-2),
  7-amino-1,3-naphthalenedisulfonic acid, potassium salt (CAS Registry No. 79873-35-1),
  4-amino-5-hydroxy-2,7-naphthalenedisulfonic acid (CAS Registry No. 90-20-0),
  5-dimethylamino-1-naphthalenesulfonic acid (CAS Registry No. 4272-77-9),
  1-amino-4-naphthalene sulfonic acid (CAS Registry No. 84-86-6),
  1-amino-7-naphthalene sulfonic acid (CAS Registry No. 119-28-8), and 2,6-naphthalenedicarboxylic acid, dipotassium salt (CAS Registry No. 2666-06-0),
3,4,9,10-perylenetetracarboxylic acid (CAS Registry No. 81-32-3),
Phorwite CL (CAS Registry No. 12270-53-0, aka Flu. Bright. 191),
Phorwite BKL (CAS Registry No. 61968-72-7, aka Flu. Bright. 200),
Phorwite BHC 766 (CAS Registry No. 52237-03-3),
Pylaklor White S-15A (CAS Registry No. 6416-68-8),
1,3,6,8-pyrenetetrasulfonic acid, tetrasodium salt (CAS Registry No. 59572-10-0),
pyranine, (CAS Registry No. 6358-69-6, aka 8-hydroxy-1,3,6-pyrenetrisulfonic acid, trisodium salt),
quinoline (CAS Registry No. 91-22-5),
Rhodalux (CAS Registry No. 550-82-3),
Rhodamine WT (CAS Registry No. 37299-86-8),
Safranine O (CAS Registry No. 477-73-6),
Sandoz CW (CAS Registry No.56509-06-9, aka Flu. Bright, 235),
Sandoz CD (CAS Registry No. 16470-24-9, aka Flu. Bright. 220),
Sandoz TH-40 (CAS Registry No. 32694-95-4),
Sulforhodamine B (CAS Registry No. 3520-42-1, aka Acid Red 52),
Tinopal 5BM-GX (CAS Registry No. 169762-28-1),
Tinopol DCS (CAS Registry No. 205265-33-4),
Tinopal CBS-X (CAS Registry No. 27344-41-8),
Tinopal RBS 200,
Titan Yellow (CAS Registry No. 1829-00-1, aka Thiazole Yellow G), and
any existing ammonium, potassium and sodium salts thereof.

The preferred fluorescent tracers are 1,3,6,8-pyrenetetrasulfonic acid, tetrasodium salt and 1,5-naphthalenedisulfonic acid, disodium salt (hydrate).

These non-toxic, fluorescent tracers are available from chemical supply companies such as ALDRICH and LANCASTER. Certain of these non-toxic fluorescent tracers are available from Nalco under the names TRASAR® 22199 for 1,5-naphthalenedisulfonic acid, disodium salt (hydrate) and
TRASAR® 23299 for 1,3,6,8-pyrenetetrasulfonic acid, tetrasodium salt.

The amount of non-toxic fluorescent tracer to use depends on the distance of the testing location from the building and the amount of fluorescent tracer required to be added to the storm drains to generate a detectable amount or "spike". The "spike" must be separately detectable as compared to whatever background fluorescence is present in the water. Typically the operator of the fluorometer will "zero out" the fluorometer using a water sample taken before any non-toxic fluorescent dye is added to the water. Then the "spike" in fluorescent signal that is observed in the presence of non-toxic fluorescent dye is used to determine the presence of non-toxic fluorescent dye. A person of ordinary skill in the art of fluorometry knows how to set up and run a fluorometer such that the fluorometer is capable of detecting the fluorescent signal of any of the non-toxic fluorescent tracers listed previously.

As stated previously, it is necessary to use enough non-toxic fluorescent tracer so that the fluorescent signal of the non-toxic fluorescent tracer is detectable over the background fluorescence of the water being tested. The background fluorescence of the water being tested varies widely, from very little to a great deal. Therefore, it is recommended, though not required, to run a sample of the water to be tested through the fluorometer before adding any non-toxic fluorescent tracer to the water. Once the background fluorescence is determined it is known to people of ordinary skill in the art of fluorescence, how much fluorescent tracer must be used such that the fluorescent signal of the non-toxic fluorescent tracer is detectable.

If time is of the essence or if it simply is desirable, it is possible to conduct the method of the instant claimed invention using an amount of fluorescent tracer such that the concentration of fluorescent tracer in the water being tested is at or above about 600 ppm. The 600 ppm figure has been found to be quite practical in testing water from many different buildings. Of course it is possible to put more non-toxic fluorescent tracer into the water than 600 ppm. It may even be desirable, with water that has a very high relative background fluorescence, to use enough non-toxic fluorescent tracer so that about 1000 ppm of non-toxic fluorescent tracer is present in the drain water.

In using a non-toxic fluorescent tracer, the non-toxic fluorescent tracer is usually first diluted in a small amount of water to prevent the fluorescent tracer from getting caught and wasted in the lip of a drain. The drain is then flushed with about 5 gallons of pure water to push the fluorescent tracer through any traps that might be present.

If a non-toxic fluorescent tracer is used in conducting Step 4 of the method of the instant claimed invention, water from a storm manhole must be continuously pumped through a suitable fluorometer capable of detecting the fluorescent signal of the fluorescent tracer. If there is not enough water in the storm manhole to pump, then it is necessary to run water continuously through the storm manhole so that there is enough water in the storm manhole to withdraw a sample for testing. The continuous running of water can be accomplished by selecting a storm drain that is known to run to the storm manhole and running water through that storm drain.

If a non-toxic fluorescent tracer is used in conducting Step (4) of the method of the instant claimed invention a fluorometer is used to detect the emitted fluorescent signal of the non-toxic fluorescent tracer. Suitable fluorometers for this purpose are available from Nalco. The preferred fluorometer is a Trasar® 3000 fluorometer (hereinafter "the Unit"), available from Nalco. The Unit is preferably configured with valving so that the flow rate though the Unit is adjustable. Adjustable flow rate can become important as the flow through the Unit represents the amount of sample taken from the manhole. This sample size is important because the size of the sample (flow rate) and the amount of dye that is added to the upstream drain influence the size and curve of the "spike" which occurs on the graph, plotting the amount of fluorescence in parts per million per second of time. The Unit also records the actual time that the measurement was taken.

Any fluorometer used must be set up so that a sample of water from the test location, can be continuously run through the fluorometer. With the Unit, it is possible to configure the Unit, using a small, commercially available portable pump, such that a sample of water from the test location can be run through the Unit continuously. It is important to note when conducting the method of the instant claimed invention that it has been found that the initial surges of water through the Unit will have higher background fluorescence levels than the water that later flows through the piping.

In conducting Step (4) of the method of the instant claimed invention, if the tracer put into any storm drain is not detected in the storm water manhole, this indicates that there may be a direct drain of the storm water into the ground or the storm drain flows in an unwanted "cross-connection" to the sanitary drain system or the storm drain flows into another, hitherto, unidentified storm manhole. One of the techniques to test the storm drains further can be tried if dye put into the storm drain being tested is not found in the storm drain manhole closest to the building then additional testing can be done by moving the point at which the dye is "looked for" in the storm drainage system downstream of the manhole that was first tested. It has been found, in conducting the method of the instant claimed invention, that often times storm drains will be connected downstream of the manhole that they were designed to flow to. The checking of storm drains draining into manholes downstream from where they should drain may continue until it no longer seems reasonable to do so.

If certain of the storm drains are not detected in any of the local storm manholes, additional testing can be conducted to see if those certain storm drains flow into any of the near-by sanitary manholes. This can be done by moving the test location from the storm manhole to the sanitary manhole and using a non-toxic fluorescent dye in the storm drain and using the fluorometer to determine whether the non-toxic fluorescent dye can be found in the sanitary manhole.

If certain of the storm drains are not detected to flow to the sanitary drain system, and all other options have been exhausted, it can be reasonably assumed that the storm drains discharge directly into the ground. This has been found to be the case in some of the older buildings that have been tested using the method of the instant claimed invention.

When the testing from Step (4) of the instant claimed method has been completed, all results should be recorded on the Master Blueprint and Master Spreadsheet. If anything is detected that contradicts the design (storm drain to sanitary, storm drain to different manhole than designed) or the blueprints, it should be clearly noted and reported on the Master Blueprint, in the Master Spreadsheet and in any Summary Document prepared summarizing what was found when the method of the instant claimed invention was conducted.

After the storm water to storm manhole drainage pattern has been determined in Step (4), Step (5) in the process of the instant claimed invention is to select the proper test location to withdraw a sample of water from. The test location is selected from the group consisting of all storm manholes and all sanitary manholes. When looking for cross-connections between storm drains and sanitary piping, then the test location should be a sanitary manhole. When looking for cross-connections between sanitary drains and storm piping, then the test location should be a storm manhole.

Step (6) in the process of the instant claimed invention is to run water continuously through a storm drain that drains into the storm manhole, providing that it is that storm manhole that is the test location selected in Step (5). Alternatively, water should be run continuously through a sanitary drain that drains into the sanitary manhole, providing that the sanitary manhole is the test location selected in the Step (5). This running of water is required in order to make sure there is always sufficient water present in the test location so that a steady sample stream may be removed from the test location and run through the fluorometer. It is important to note that storm manholes are supposed to be absolutely dry except during periods of rain and sanitary manholes do not always have material in them either. It has been found when conducting the method of the instant claimed invention that nearly all of the manholes are dry when it is not raining. Of course the Method of the instant claimed invention cannot work if it is not possible to pump water out of the manhole to put through the Unit.

To ensure that there is a proper flow of water through manholes, water can be added continuously with water hoses to the storm drain that takes the longest amount of time to drain to the storm manhole that is the test location within the building drainage system. This ensures that any water (and non-toxic fluorescent tracer) that is introduced via a drain is flushed to the manhole being tested. Of course if the test location is a sanitary manhole, then water can be run continuously through the sanitary drain that takes the longest amount of time to drain to the sanitary manhole that is the test location.

Step (7) in the process of the instant claimed invention is the selection of a target sanitary drain for testing. The target sanitary drain is tested by adding a non-toxic fluorescent tracer to the drain and flushing the target drain continuously with water from the hose. When the non-toxic fluorescent tracer is detected by the Unit, the next target sanitary drain is tested in the same manner.

As was the case in Step (4), if a fluorescent tracer was used, in using a non-toxic fluorescent tracer, the non-toxic fluorescent tracer is usually first diluted in a small amount of water to prevent the fluorescent tracer from getting caught and wasted in the lip of a drain. The drain is then flushed with about 5 gallons of pure water to push the fluorescent tracer through any traps that might be present.

The non-toxic fluorescent tracer chosen is selected from the group consisting of those materials previously identified in the description of Step (4) as being suitable fluorescent tracers. The preferred non-toxic fluorescent tracers for use in Step (7) of the instant claimed invention are 1,3,6,8-pyrenetetrasulfonic acid, tetrasodium salt and 1,5-naphthalenedisulfonic acid, disodium salt (hydrate).

As was stated in the description of Step (4) the amount of non-toxic fluorescent tracer used in Step (7) depends on the distance of the testing location from the building and the amount of fluorescent tracer added to the storm drains to generate a detectable amount or "spike". It is necessary to use enough non-toxic fluorescent tracer so that the fluorescent signal of the non-toxic fluorescent tracer is detectable over the background fluorescence of the water being tested. The background fluorescence of the water being tested varies widely, from very little to a great deal. The background fluorescence of grey water (water in a sanitary drainage system that contains no human waste products, yet does contain drain water from other sources) would be expected to be greater than that of storm water, though not as high as the background fluorescence of drains containing human waste products.

Therefore, it is recommended, though not required, to run a sample of the water to be tested through the fluorometer before adding any non-toxic fluorescent tracer to the water. Once the background fluorescence is determined it is known to people of ordinary skill in the art of fluorometry, how much fluorescent tracer must be used such that the fluorescent signal of the non-toxic fluorescent tracer is detectable.

As was stated in the description of Step (4) if time is of the essence or if it simply is desirable, it is possible to conduct the method of the instant claimed invention using an amount of fluorescent tracer such that the concentration of fluorescent tracer in the water being tested is at or above about 600 ppm. The 600 ppm figure has been found to be quite practical in testing water from many different buildings.

As was stated in the description of Step (4), preferably, the fluorescent tracer is first diluted in a small amount of water to prevent the fluorescent tracer from getting caught in the lip of a drain. The drain is then flushed with about 5 gallons of pure water to push the fluorescent tracer through any traps that might be present.

As was stated in the description of Step (4), water from the drain is continuously pumped through a suitable fluorometer capable of detecting the fluorescent signal of the fluorescent tracer. Suitable fluorometers are available from Nalco. The preferred fluorometer is a Trasar® 3000 fluorometer (hereinafter "the Unit"), available from Nalco. The Unit is preferably configured with valving so that the flow rate though the Unit is adjustable. Adjustable flow rate can become important as the flow through the Unit represents the amount of sample taken from the manhole. This sample size is important because the size of the sample (flow rate) and the amount of dye that is added to the upstream drain influence the size and curve of the "spike" which occurs on the graph, plotting the amount of fluorescence in parts per million per second of time. The Unit also records the actual time that the measurement was taken.

Step (8) of the instant claimed invention involves using a fluorometer to detect the fluorescent signal of said non-toxic fluorescent tracer in the sample of water withdrawn at the test location selected in Step (5). The preferred fluorometer is the Unit. It is important to note that even though use of The Unit is preferred in Step (8), because it can automatically record and manipulate data, it is possible to conduct the method of the instant claimed invention by using a different fluorometer and manually recording the information detected by the fluorometer.

One of the reasons the use of the Unit is preferred is because when the Unit is in the preferred configuration where it records information every second, the Unit currently can store data for about 5 hours and 20 minutes before the data must be downloaded.

In conducting Step (7) and Step (8) of the method of the instant claimed invention every time non-toxic fluorescent tracer is added to a drain, the time should be recorded in a "test log sheet". One possible TEST LOG SHEET is as follows:

| TEST LOG SHEET for Fuzzybuilding and Smoothbuilding Cross Over Connection Study | | | |
|---|---|---|---|
| Fuzzbldg and Smoothbldg Survey | UP | Water Continuously Added to Which Drains? (in order to ensure adequate passage of water through the storm water system so that the Unit is always registering a fresh sample) | 134, 141 |
| Building | Fuzzybldg | DataLogger Erased | yes |
| Fuzzbldg Number | 2010404 | Time DataLogger Started | 12:53 p |
| Test Number | 7 | Time to Stop Adding fluorescent tracer | 5:30 p |
| Date | yesterday | Time DataLogger to be Shut Down | 6:20 p |
| Workers | Bob and Bill | Actual Time DataLogger Turned Off | 5:17 p |
| First Manhole Tested | bus stop | Hours & Minutes DataLogger Operated | 4 hrs 24 min |
| Second Manhole Tested (needed if building has more than one storm drain system) | | Time on watch | 12:52 p |
| Rooms with No Access | | Time on DataLogger | 12:52 p |

This next table is a sample page from a Master Spreadsheet used to mark down the time non-toxic fluorescent tracer is added to each drain. This time is then compared to when the "spike" of fluorescent signal is detected in the sample location and this information used to determine if the drain is draining to where it is supposed to be draining or it is cross-connected in error:

| Drains Where Fluorescent tracer Was Added | |
|---|---|
| Drain ID | Time |
| 56 | 1:28 p |
| 55 | 1:37 p |
| 149 | 1:41 p |
| 70 | 1:46 p |
| 72 | 1:49 p |
| 83 | 2:06 p |
| 91 | 2:14 p |
| 92 | 2:18 p |
| 85 | 2:24 p |
| 86 | 2:24 p |
| 84 | 2:27 p |
| 93 | 2:33 p |
| 98 | 2:57 p |
| 100 | 3:07 p |
| 101 | 3:07 p |
| 99 | 3:17 p |
| 144 | 3:36 p |
| 104 | 3:37 p |
| 109 | 4:01 p |
| 110 | 3:59 p |
| 123 | 4:20 p |
| 124 | 4:18 p |
| 122 | 4:28 p |
| 118 | 4:29 p |

As stated previously, when configured to record data every second, the Unit can store data for about 5 hours and 20 minutes before the data must be downloaded to a computer. This gives the test operator about 5 hours to add non-toxic fluorescent tracer to drains. Non-toxic fluorescent tracer is added to as many drains as possible during the 5-hour period. Once the operating time of The Unit is up, the data can be downloaded onto a computer and can be analyzed to glean useful information from the test.

Of course, it is possible to configure the Unit to record data at different time intervals instead of every second.

It is also important to note that the flow rate through the manhole, the flow rate provided by the sump pump (that pushes the water through the Unit), the amount of non-toxic fluorescent dye that is added at the drain being tested, the amount of water that is used to flush the dye through the traps, the size of the piping being tested, the length of piping between the drain being tested and the manhole, all affect the "curve" that is generated using the Unit's DataLogger program. This curve can be used to determine which readings are true "spikes" and which readings are false background readings.

Step (9) of the instant claimed invention involves using the fluorescent signal to determine whether the target sanitary drain is draining to the test location selected in Step (5), or is cross-connected in error, and then recording the information determined about the flow pattern of said sanitary drain on the Master Blueprint and on the Master Spreadsheet. This information will then be reported on the Master Spreadsheet and Master Blueprint of the building.

Step (10) of the instant claimed invention is repeating Steps (4), (5), (6), (7), (8) and (9) as necessary such that all sanitary drains are traced.

Step (11) involves using the information from the Master Blueprint and Master Spreadsheet to determine where all sanitary drains and storm drains are draining.

In conducting this method, it is common to find drains that are not draining to where they are supposed to be draining. Additional testing is necessary to determine where these mis-connected or "cross-connected" drains are draining. This part of the method focuses on finding the drains that are cross-connected. After it has been determined that putting non-toxic fluorescent tracer into one of the tested sanitary drains generated a "spike" of fluorescent signal in the storm system, the following factors can be used to hypothesize, analyze and attempt to determine which drain or drains could possibly have caused the "spike" in fluorescent signal detected:

i) the time non-toxic fluorescent tracer was added to each sanitary drain;
ii) the time the detectable "spike" of fluorescent signal was detected;
iii) the time it "normally" takes for roof drains to record a detectable "spike" of fluorescent signal (determined from Step (4) of the instant claimed method); and
iv) Other factors based on the configuration of the actual drains.

If it is found that at least one of the sanitary drains were connected to the storm water drainage system, (for example, if the normal fluorescence reading is less than twenty, and a spike of over 600 ppm is detected in the storm water drainage system) it will be necessary for the operator to go back and review the drains tested for each of the above-described factors. This review can be conducted in many possible ways. One such way is to assume that roof drains took a specific amount of time for their tracer signal to be detected (or to "spike" as it is commonly described), it is reasonable to think that the sanitary drain would take approximately the same time for its fluorescent signal based on the non-toxic fluorescent dye added to be detected. This is where it is helpful to review the daily log to determine which drains fall into this time frame. However, other facts can also be considered when using this method during testing. For example, if water could be heard flowing at a specific drain (floor drain), it may be that the water heard might be the water that was being supplied to the roof drains to provide constant flow to the storm water manhole. This theory can be used to hypothesize that a specific drain was the drain that originally spiked. Once a hypothesis is in place, the next step is to retest the drain by itself to see if it spikes again as predicted. After concluding this review, the operator of the method will have selected the drain that is believed to be most likely to be the cross-connected drain.

Retesting a drain can be done using the exact procedure described above, except only one drain is tested at a time to make sure that the spike is indeed coming from the drain that is thought to be cross-connected. If the drain spikes in about the same time frame as the first test, it is concluded that the drain is indeed cross connected. If no spike occurs after an extended period of time, than the next most probable drain is tested. After a certain drain is identified as draining to the storm drains than the operator must determine whether other drains also drain to the storm drains.

If any drains are tested about the same time as the cross-connected drain, it is possible that the spikes could blend together. Therefore, all of the drains done at approximately the same time should ideally be retested to see if any more spikes in detectable fluorescent signal develop.

When the method is concluded it is recommended to summarize all of the findings in a report with drawings. The report should describe any drains that were found to be cross-connected, any mislabeled manholes, any discrepancies that were found between the drawings and what was actually constructed, as well as anything else of note to the owner of the building.

In this report, problem drains should be unambiguously identified. One such nomenclature system for identifying problem drains is as follows:

"ccd" for cross-connected drain

"bd" for bad drain or clogged drain

"ud" for unplumbed drain (uncommon, but has been found more than once)

After completing Step (11) of the method of the instant claimed invention it will be possible to instruct plumbers as to where and what type of repairs are required. After the repairs have been implemented the method of the instant claimed invention can be conducted again, to verify that the correct repairs have been made.

This method, when conducted correctly, is extremely reliable and repeatable. The process and equipment work very well.

What is claimed is:

1. A method of tracing drains in a building comprising:
   (1) surveying the building to locate all existing drains;
   (2) numbering all of the existing drains;
   (3) creating a Master Blueprint and a Master Spreadsheet showing all of the drains;
   (4) using a tracer to determine whether the storm water from the building actually flows from each storm drain to the storm water manhole and recording the information determined about the flow pattern of each storm drain tested on the Master Blueprint and on the Master Spreadsheet;
   (5) selecting the test location to withdraw the sample of water, wherein said test location is selected from the group consisting of all storm manholes and all sanitary manholes;
   (6) running water continuously through a drain that drains into the test location manhole selected in Step (5);
   (7) selecting a target sanitary drain and adding an amount of non-toxic fluorescent tracer to the target sanitary drain, wherein the amount of non-toxic fluorescent tracer added is such that the fluorescent signal of non-toxic fluorescent tracer is detectable over the background fluorescence of the water in said sanitary drain;
   (8) using a fluorometer to detect the fluorescent signal of said non-toxic fluorescent tracer in the sample of water withdrawn at the test location selected in Step (5);
   (9) using the fluorescent signal to determine whether the target sanitary drain is draining to the test location selected in Step (5) and recording the information determined about the flow pattern of said target sanitary drain on the Master Blueprint and on the Master Spreadsheet;
   (10) repeating Steps (4), (5), (6), (7), (8) and (9) as necessary such that all sanitary drains are traced; and
   (11) using the information from the Master Blueprint and Master Spreadsheet to determine where all sanitary drains and storm drains are draining.

2. The method of claim 1 further comprising:
   (12) effecting repairs to the building such that the drains tested are configured such that they drain to their intended location.

3. The method of claim 2 further comprising:
   (13) retesting the drains using the method of Steps (4) through (11) to ensure that all drains are now draining to their intended location.

4. The method of claim 1 in which the tracer used in Step (4) is a visible dye tracer and the non-toxic fluorescent tracer used in Step (7) is selected from the group consisting of 1,3,6,8-pyrenetetrasulfonic acid, tetrasodium salt and 1,5-naphthalenedisulfonic acid, disodium salt.

5. The method of claim 1 in which the drain chosen in Step (6) to run water continuously through is the drain that takes the longest amount of time to drain to the test location manhole.

6. A method of tracing drains in a building comprising:
   (1) surveying the building to locate all existing drains;
   (2) numbering all of the existing drains;
   (3) creating a Master Blueprint and a Master Spreadsheet showing all of the drains;
   (4) using a tracer to determine whether the storm water from the building actually flows from each storm drain to the storm water manhole and recording the information determined about the flow pattern of each storm drain tested on the Master Blueprint and on the Master Spreadsheet;
   (5) selecting the test location to withdraw the sample of water, wherein said test location is selected from the group consisting of all storm manholes and all sanitary manholes;
   (6) running water continuously through a drain that drains into the test location manhole selected in Step (5);
   (7) selecting a target sanitary drain and adding an amount of non-toxic fluorescent tracer to the target sanitary drain, wherein the amount of non-toxic fluorescent tracer added is such that the concentration of non-toxic fluorescent tracer is at least about 600 ppm in the water in said target sanitary drain;
   (8) using a fluorometer to detect the fluorescent signal of said non-toxic fluorescent tracer in the sample of water withdrawn at the test location selected in Step (5);
   (9) using the fluorescent signal to determine whether the target sanitary drain is draining to the test location selected in Step (5) and recording the information determined about the flow pattern of said target sanitary drain on the Master Blueprint and on the Master Spreadsheet;
   (10) repeating Steps (4), (5), (6), (7), (8) and (9) as necessary such that all sanitary drains are traced; and
   (11) using the information from the Master Blueprint and Master Spreadsheet to determine where all sanitary drains and storm drains are draining.

7. The method of claim 6 further comprising:
(12) effecting repairs to the building such that the drains tested are configured such that they drain to their intended location.

8. The method of claim 7 further comprising:
(13) retesting the drains using the method of Steps (4) through (11) to ensure that all drains are now draining to their intended location.

9. The method of claim 6 in which the tracer used in Step (4) is a viable dye tracer and then non-toxic fluorescent tracer used in Step (7) is selected from the group consisting of 1,2,6,8-pyrenetetrasulfonic acid, tetrasodium salt and 1,5-naphthalenedisulfonic acid, disodium salt.

10. The method of claim 6 in which the drain chosen in Step (6) to run water continuously through is the drain that takes the longest amount of time to drain to the test location manhole.

11. A method of tracing drains of interest in a building comprising:
(1) surveying the building to locate the drains of interest;
(2) numbering all of the drains of interest;
(3) creating a Master Blueprint and a Master Spreadsheet showing all of the drains of interest;
(4) using a tracer to determine whether the storm water from the building actually flows from the storm drains of interest to the storm water manhole and recording the information determined about the flow pattern of each storm drain tested on the Master Blueprint and on the Master Spreadsheet;
(5) selecting the test location to withdraw the sample of water, wherein said test location is selected from the group consisting of all storm manholes and all sanitary manholes;
(6) running water continuously through a drain that drains into the test location manhole selected in Step (5);
(7) selecting a target sanitary drain of interest and adding an amount of non-toxic fluorescent tracer to the target sanitary drain of interest, wherein the amount of non-toxic fluorescent tracer added is such that the fluorescent signal of non-toxic fluorescent tracer is detectable over the background fluorescence of the water in said target sanitary drain of interest;
(8) using a fluorometer to detect the fluorescent signal of said non-toxic fluorescent tracer in the sample of water withdrawn at the test location selected in Step (5);
(9) using the fluorescent signal to determine whether the target sanitary drain of interest is draining to the test location selected in Step (5) and recording the information determined about the flow pattern of said target sanitary drain of interest on the Master Blueprint and on the Master Spreadsheet;
(10) repeating Steps (4), (5), (6), (7), (8) and (9) as necessary such that all sanitary drains of interest are traced; and
(11) using the information from the Master Blueprint and Master Spreadsheet to determine where the sanitary drains of interest and the storm drains of interest, are draining.

12. The method of claim 11 further comprising:
(12) effecting repairs to the building such that the drains tested are configured such that they drain to their intended location.

13. The method of claim 12 further comprising:
(13) retesting the drains using the method of Steps (4) through (11) to ensure that all drains are now draining to their intended location.

14. The method of claim 11 in which the tracer used in Step (4) is a visible dye tracer and the non-toxic fluorescent tracer used in Step (7) is selected from the group consisting of 1,3,6,8-pyrenetetrasulfonic acid, tetrasodium salt and 1,5-naphthalenedisulfonic acid, disodium salt.

15. The method of claim 11 in which the drain chosen in Step (6) to run water continuously through is the drain that takes the longest amount of time to drain to the test location manhole.

16. A method of tracing drains of interest in a building comprising:
(1) surveying the building to locate the drains of interest;
(2) numbering all of the drains of interest;
(3) creating a Master Blueprint and a Master Spreadsheet showing all of the drains of interest;
(4) using a tracer to determine whether the storm water from the building actually flows from the storm drains of interest to the storm water manhole and recording the information determined about the flow pattern of each storm drain tested on the Master Blueprint and on the Master Spreadsheet;
(5) selecting the test location to withdraw the sample of water, wherein said test location is selected from the group consisting of all storm manholes and all sanitary manholes;
(6) running water continuously through a drain that drains into the test location manhole selected in Step (5);
(7) selecting a target sanitary drain of interest and adding an amount of non-toxic fluorescent tracer to the target sanitary drain of interest, wherein the amount of non-toxic fluorescent tracer added is such that the concentration of non-toxic fluorescent tracer is at least about 600 ppm in the water in said target sanitary drain of interest;
(8) using a fluorometer to detect the fluorescent signal of said non-toxic fluorescent tracer from the sample of water withdrawn at the test location selected in Step (5);
(9) using the fluorescent signal to determine whether the target sanitary drain of interest is draining to the test location selected in Step (5) and recording the information determined about the flow pattern of said target sanitary drain of interest on the Master Blueprint and on the Master Spreadsheet;
(10) repeating Steps (4), (5), (6), (7), (8) and (9) as necessary such that all sanitary drains of interest are traced;
(11) using the information from the Master Blueprint and Master Spreadsheet to determine where the sanitary drains of interest and the storm drains of interest are draining.

17. The method of claim 16 further comprising:
(12) effecting repairs to the building such that the drains tested are configured such that they drain to their intended location.

18. The method of claim 17 further comprising:
(13) retesting the drains using the method of Steps (4) through (11) to ensure that all drains are now draining to their intended location.

19. The method of claim 16 in which the tracer used in Step (4) is a visible dye tracer and the non-toxic fluorescent tracer used in Step (7) is selected from the group consisting of 1,3,6,8-pyrenetetrasulfonic acid, tetrasodium salt and 1,5-naphthalenedisulfonic acid, disodium salt.

20. The method of claim 16 in which the drain chosen in Step (6) to run water continuously through is the drain that takes the longest amount of time to drain to the test location manhole.

* * * * *